(12) United States Patent
Shabbat

(10) Patent No.: US 9,707,150 B2
(45) Date of Patent: Jul. 18, 2017

(54) GASTROINTESTINAL CAPSULE AND TREATMENT METHOD

(71) Applicant: Ronny Shabbat, Kibbutz Yizra'el (IL)

(72) Inventor: Ronny Shabbat, Kibbutz Yizra'el (IL)

(73) Assignee: VIBRANT LTD., Yokneam (IL)

( * ) Notice: Subject to any disclaimer, the term of this patent is extended or adjusted under 35 U.S.C. 154(b) by 257 days.

(21) Appl. No.: 14/461,414

(22) Filed: Aug. 17, 2014

(65) Prior Publication Data

US 2015/0073315 A1 Mar. 12, 2015

Related U.S. Application Data

(63) Continuation-in-part of application No. PCT/IB2013/000203, filed on Feb. 17, 2012.
(Continued)

(30) Foreign Application Priority Data

Feb. 16, 2012 (GB) .................................. 1202706.6

(51) Int. Cl.
*A61H 23/02* (2006.01)
*A61B 1/00* (2006.01)
*A61H 21/00* (2006.01)

(52) U.S. Cl.
CPC ......... *A61H 23/02* (2013.01); *A61B 1/00156* (2013.01); *A61H 21/00* (2013.01);
(Continued)

(58) Field of Classification Search
CPC ........ A61H 2205/083; A61H 2201/149; A61H 2201/1207; A61H 2201/0157;
(Continued)

(56) References Cited

U.S. PATENT DOCUMENTS

2003/0020810 A1 1/2003 Takizawa et al.
2005/0085696 A1 4/2005 Uchiyama et al.
(Continued)

FOREIGN PATENT DOCUMENTS

CN          1829466 A     9/2006
IL   WO 2008035329 A2 *  3/2008  ............. A61H 23/02
(Continued)

OTHER PUBLICATIONS

International Search Report for PCT/IB2013/000203 dated Jun. 27, 2013, published as WO/2013/121276.
(Continued)

*Primary Examiner* — Justine Yu
*Assistant Examiner* — Daniel Garbus
(74) *Attorney, Agent, or Firm* — Marc Van Dyke; Fourth Dimension IP

(57) ABSTRACT

A gastrointestinal capsule (GIC) including a capsule housing having a longitudinal axis; a thrusting mechanism, disposed within the housing; and a battery adapted to power the and a battery adapted to power the thrusting mechanism; the thrusting mechanism having an active mode, and a passive mode with respect to the active mode, the thrusting mechanism adapted to exert a radial force on the housing, in a radial direction with respect to the axis, such that when the capsule is disposed within a gastrointestinal tract of a user, and the mechanism is in the active mode, the gastrointestinal capsule stimulates a wall of the tract; the active mode including a series of at least two pulses of the radial force, the series having a first duration, the passive mode having a second duration, wherein an activation cycle is defined by the series of pulses followed by the second duration.

19 Claims, 6 Drawing Sheets

Related U.S. Application Data

(60) Provisional application No. 61/930,972, filed on Jan. 24, 2014.

(52) U.S. Cl.
CPC ..... *A61H 23/0254* (2013.01); *A61H 23/0263* (2013.01); *A61H 2201/1207* (2013.01); *A61H 2201/149* (2013.01); *A61H 2205/083* (2013.01)

(58) Field of Classification Search
CPC ........ A61H 2201/12; A61H 2201/1215; A61H 2201/1481; A61H 2201/50; A61H 2201/5007; A61B 1/00156
See application file for complete search history.

(56) References Cited

U.S. PATENT DOCUMENTS

| | | | | |
|---|---|---|---|---|
| 2005/0177069 | A1* | 8/2005 | Takizawa | A61B 1/041 600/573 |
| 2007/0015952 | A1* | 1/2007 | Chang | A61H 21/00 600/29 |
| 2007/0238940 | A1* | 10/2007 | Amirana | A61B 5/06 600/302 |
| 2008/0161639 | A1* | 7/2008 | Katayama | A61B 1/041 600/104 |
| 2009/0318841 | A1 | 12/2009 | Shohat et al. | |
| 2010/0217079 | A1 | 8/2010 | Tichy | |

FOREIGN PATENT DOCUMENTS

| | | |
|---|---|---|
| JP | 2001062397 A | 3/2001 |
| JP | 2010503451 A | 2/2010 |
| WO | 2008035329 A2 | 3/2008 |

OTHER PUBLICATIONS

Written Opinion for PCT/IB2013/000203 dated Jun. 27, 2013, published as WO/2013/121276.
JP 2010503451 Machine Translation (by EPO and Google)—published Feb. 4, 2010; Vibrant Ltd.
JP 2001062397 Machine Translation (by EPO and Google)—published Mar. 13, 2001; Japan Aviation Electronics Industry Ltd.
CN 1829466 Machine Translation (by EPO and Google)—published Sep. 6, 2006; Olympus Corp.
First Office Action Translation from SIPO (State Intellectual Property Office) of PRC—CN Application No. 201380020227.6 dated Dec. 31, 2015.
Patent Examination Report from Australian Patent Office AU—Application No. 2014224165, dated Oct. 24, 2016.
First Office Action Translation from JPO Japanese Patent Office—JP Application No. 2014-557129, dated Nov. 29, 2016.

* cited by examiner

GASTROINTESTINAL CAPSULE AND TREATMENT METHOD

CROSS-REFERENCE TO RELATED APPLICATIONS

U.S. Provisional Patent Application Ser. No. 61/930,972, filed Jan. 24, 2014 is incorporated herein by reference in its entirety. In some embodiments, any feature or combination of features described in the present document may be combined with any feature of combination of features described in U.S. Provisional Patent Application Ser. No. 61/930,972.

PCT Application No. PCT/IB2013/000203, filed Feb. 17, 2013 is incorporated herein by reference in its entirety. In some embodiments, any feature or combination of features described in the present document may be combined with any feature of combination of features described in application PCT/IB2013/000203.

British Patent Application No. GB1202706.6, filed Feb. 16, 2012 is incorporated herein by reference in its entirety. In some embodiments, any feature or combination of features described in the present document may be combined with any feature of combination of features described in British Patent Application No. GB1202706.6.

U.S. Provisional Patent Application Ser. No. 61/602,093, filed Feb. 23, 2012 is incorporated herein by reference in its entirety. In some embodiments, any feature or combination of features described in the present document may be combined with any feature of combination of features described in U.S. Provisional Patent Application Ser. No. 61/602,093.

FIELD AND BACKGROUND OF THE INVENTION

The present invention relates to gastrointestinal capsules (GICs).

Intestinal constipation is a widespread gastrointestinal motility disorder. Various treatment programs are known, employing dietary modifications and supplements, laxatives, and suppositories. In severe cases, surgery may be indicated. Constipation may be considered a symptom, and care must be taken, in treating the symptom, not to exacerbate or aggravate the general condition of the patient. Thus, by way of example, the frequent or long-term use of laxatives may be detrimental, as such laxatives may compromise the ability of the body to independently effect bowel movements.

An ingestible gastrointestinal capsule for mechanically stimulating a segment of the gastrointestinal wall is disclosed by U.S. Patent Publication No. 20090318841, which is incorporated by reference for all purposes as if fully set forth herein.

However, the present inventor has recognized a need for improved gastrointestinal capsules and treatment methods utilizing such capsules.

SUMMARY OF THE INVENTION

According to the teachings of the present invention there is provided a gastrointestinal capsule (GIC) including: (a) a capsule housing having a longitudinal axis; (b) at least one thrusting mechanism, disposed within the housing, the thrusting mechanism adapted to exert radial forces on the housing, in a radial direction with respect to the axis, such that, when the capsule is disposed within a gastrointestinal tract of a user, and the mechanism is in an active mode, the gastrointestinal capsule exerts forces against, or in a direction of the walls of the tract; and (c) a power supply adapted to power the mechanism, wherein a ratio of the radial forces to axial forces exerted in an axial direction with respect to the axis, on the housing, by the thrusting mechanism, is at least 1:1, at least 1.25:1, at least 1.5:1, at least 2:1, at least 3:1, at least 4:1, or at least 5:1.

According to yet another aspect of the present invention there is provided a gastrointestinal capsule including: (a) a housing; (b) a thrusting mechanism, disposed within the housing, the mechanism having an active mode and a passive mode, with respect to the active mode, the mechanism adapted to exert a radial force on the housing, whereby, when the capsule is disposed within a gastrointestinal tract of a user, and the mechanism is in the active mode, the gastrointestinal capsule stimulates the walls of the tract; and (c) a battery adapted to power the mechanism, wherein the active mode includes a series of at least two pulses of the radial force, the series having a first duration, the passive mode has a second duration, and wherein an activation cycle is defined by the series of pulses followed by the second duration, and wherein the first duration is within a range of 1-10 seconds.

According to still further features in the described preferred embodiments, the ratio is at most 20:1, at most 12:1, at most 10:1, at most 8:1, at most 7:1, or at most 6:1.

According to still further features in the described preferred embodiments, the ratio is within a range of 1:1 to 15:1, 2.5:1 to 15:1, 2.5:1 to 10:1, 2.5:1 to 8:1, or 2.5:1 to 6:1.

According to still further features in the described preferred embodiments, the at least one thrusting mechanism includes an axial perturbation arrangement having: (i) a motor electrically connected to the power supply; and (ii) an urging mechanism, associated with, and driven by, the motor, the urging mechanism adapted to exert the axial forces.

According to still further features in the described preferred embodiments, the urging mechanism includes: a motor shaft, disposed at least partially in a direction along the longitudinal axis, the shaft being operatively connected to, and driven by, the motor; and a thrusting weight associated with the shaft, the urging mechanism further adapted to at least periodically urge the weight along the shaft, to deliver the axial forces.

According to still further features in the described preferred embodiments, the urging mechanism further includes a stopper or cap, adapted to receive a distal end of the shaft, the stopper or cap impinging against an inner wall of the capsule housing.

According to still further features in the described preferred embodiments, the urging mechanism further includes a spring associated with the motor shaft, the urging mechanism being adapted such that, in a first state, the spring is compressed, and such that, in a second state, the spring is released against the weight, to urge the weight along the shaft, to deliver the axial forces against the capsule housing.

According to still further features in the described preferred embodiments, the motor shaft passes through the weight, the motor shaft has an external interrupted thread, and the weight has a threaded internal surface generally complementary to a threading of the interrupted thread, whereby, in the first state, the external interrupted thread engages the threaded internal surface, and in the second state, the threaded internal surface is disengaged and longitudinally free with respect to the interrupted thread.

According to still further features in the described preferred embodiments, the motor shaft passes through the weight, the weight being adapted to turn with the shaft, the motor shaft having an external interrupted thread, and the weight having a threaded internal surface generally complementary to a threading of the interrupted thread, the urging mechanism being further adapted such that in the first state, the external interrupted thread engages the threaded internal surface to compress the spring, and in a second state, the threaded internal surface is disengaged and longitudinally free with respect to the interrupted thread, such that the spring is released against the weight.

According to still further features in the described preferred embodiments, the thrusting mechanism includes a rotatably mounted eccenter, the thrusting mechanism being adapted to rotate the eccenter to exert the radial forces.

According to still further features in the described preferred embodiments, the thrusting mechanism is configured to have the active mode and a passive mode with respect to the active mode, the active mode including a series of at least two pulses of the radial forces, wherein the series has a first duration, the passive mode has a second duration, and wherein the second duration exceeds the first duration.

According to still further features in the described preferred embodiments, the first duration and the second duration define an activation cycle, the thrusting mechanism being configured such that the activation cycle has a period within a range of 5-60 seconds, 7-40 seconds, 8-30 seconds, 10-30 seconds, or 12-25 seconds.

According to still further features in the described preferred embodiments, the first duration and the second duration define an activation cycle, the thrusting mechanism being configured such that the activation cycle has a period of at least 5, at least 6, at least 7, at least 8, at least 10, at least 12, or at least 15 seconds, and/or at most 60, at most 40, at most 30, at most 25, or at most 20 seconds.

According to still further features in the described preferred embodiments, the thrusting mechanism is configured such that the first duration is within a range of 1-10 seconds, 2-8 seconds, or 2.5-6 seconds.

According to still further features in the described preferred embodiments, the thrusting mechanism is configured such that a net force exerted by the capsule on an external environment is at least 400 grams force, at least 450 grams force, at least 500 grams force, or at least 600 grams force.

According to still further features in the described preferred embodiments, the thrusting mechanism is configured such that the net force is an instantaneous net force of at least 800 grams force, at least 1000 grams force, at least 1200 grams force, at least 1400 grams force, or at least 1500 grams force.

According to still further features in the described preferred embodiments, the thrusting mechanism is configured to exert the radial forces on the housing to attain a vibrational frequency, of the housing, within a range of 12 Hz to 80 Hz.

According to still further features in the described preferred embodiments, the thrusting mechanism is configured such that this range is 12 Hz to 70 Hz, 15 Hz to 60 Hz, 15 Hz to 50 Hz, 18 Hz to 45 Hz, or 18 Hz to 40 Hz.

According to still further features in the described preferred embodiments, the thrusting mechanism is configured such that this vibrational frequency is at least 15 Hz, at least 18 Hz, at least 20 Hz, or at least 22 Hz.

According to still further features in the described preferred embodiments, the thrusting mechanism is configured such that this vibrational frequency is at most 75 Hz, at most 70 Hz, at most 60 Hz, at most 50 Hz, at most 45 Hz, or at most 40 Hz.

According to still further features in the described preferred embodiments, the axial arrangement is adapted to exert the axial forces in opposite directions.

According to still further features in the described preferred embodiments, the axial arrangement is adapted to deliver at least a portion of the axial forces in a knocking mode.

According to still further features in the described preferred embodiments, the thrusting mechanism has a first individual motor for delivering the radial forces and a second individual motor for delivering the axial forces.

According to still further features in the described preferred embodiments, the first individual motor and the second individual motor are disposed on different sides of the capsule, with respect to the axis.

According to still further features in the described preferred embodiments, the thrusting mechanism is adapted such that when the capsule is disposed within the tract, and the mechanism is in the active mode, the capsule stimulates the walls of the tract.

According to still further features in the described preferred embodiments, the thrusting mechanism includes a controller, electrically attached to the power supply, the controller adapted to control the thrusting mechanism.

According to still further features in the described preferred embodiments, the controller is physically isolated from all motors within the housing.

According to still further features in the described preferred embodiments, the controller is physically isolated, by at least 2 mm, from all motors within the housing.

According to still further features in the described preferred embodiments, the thrusting mechanism is adapted to exert a radial force on the housing, whereby, when the capsule is disposed within a gastrointestinal tract of a user, and the thrusting mechanism is in the active mode, the gastrointestinal capsule induces a peristaltic wave in the walls of the tract.

According to still further features in the described preferred embodiments, the length of the GIC is at most 28 mm, at most 26 mm, at most 25 mm, at most 24 mm, at most 22 mm, at most 20 mm, at most 18 mm, at most 15 mm, or at most 12 mm.

According to still further features in the described preferred embodiments, the weight of the GIC is at most 25 grams, at most 22 grams, at most 20 grams, at most 17 grams, at most 15 grams, at most 12 grams, or at most 10 grams.

According to yet another aspect of the present invention there is provided a therapeutic method for mechanically stimulating a wall of a segment of a mammalian gastrointestinal tract of a user by means of a gastrointestinal capsule, the method including: (a) providing the gastrointestinal capsule; (b) administering at least one treatment session, each treatment session including: (i) delivering the gastrointestinal capsule into the tract; and (ii) effecting activation of a thrusting mechanism of the gastrointestinal capsule to achieve mechanical stimulation of the wall of the gastrointestinal tract.

According to still further features in the described preferred embodiments, the at least one treatment session includes a plurality of the treatment sessions.

According to still further features in the described preferred embodiments, at least one of the treatment sessions is administered per week, over a treatment period extending for at least two weeks, at least three weeks, at least four weeks, at least five weeks, at least six weeks, or at least eight weeks.

According to still further features in the described preferred embodiments, at least 1.5, at least 1.75, at least 2, at least 2.5, or at least 3 of the treatment sessions is administered per week of the treatment period.

According to still further features in the described preferred embodiments, a frequency of the treatment sessions administered to the user is within a range of 1.5 to 6 per week of the treatment period.

According to still further features in the described preferred embodiments, the frequency is within a range of 1 to 7, 1.5 to 7, 1.5 to 6, 1.5 to 5, 1.5 to 4, 1.5 to 3.5, 1.5 to 3, 2 to 6, 2 to 5, 2 to 4, 2 to 3.5, or 2 to 3, per week of the treatment period.

According to still further features in the described preferred embodiments, within each the treatment session, the activation of the thrusting mechanism is performed for a duration effective to achieve the mechanical stimulation of the wall of the gastrointestinal tract.

According to still further features in the described preferred embodiments, within each treatment session, the activation of the thrusting mechanism is performed for a duration effective to increase a frequency of spontaneous bowel movements of the user.

According to still further features in the described preferred embodiments, within each treatment session, the activation of the thrusting mechanism is performed for a duration effective to increase a frequency of spontaneous bowel movements of the user by at least 25%, at least 50%, at least 75%, or at least 100%.

According to still further features in the described preferred embodiments, within each treatment session, the activation of the thrusting mechanism is performed for a duration effective to at least partially relieve, or to completely relieve, a condition of constipation of the user.

According to still further features in the described preferred embodiments, the vibration frequency and relaxation period may be varied, within a single treatment period, in order to prevent habituation.

According to still further features in the described preferred embodiments, the delivering of the GIC is performed via oral insertion.

According to still further features in the described preferred embodiments, the delivering of the GIC is performed by inserting the GIC into the tract via a rectal opening of the user.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Throughout the drawings, like-referenced characters are used to designate like elements.

In the drawings.

DESCRIPTION OF THE PREFERRED EMBODIMENTS

Figure 1:
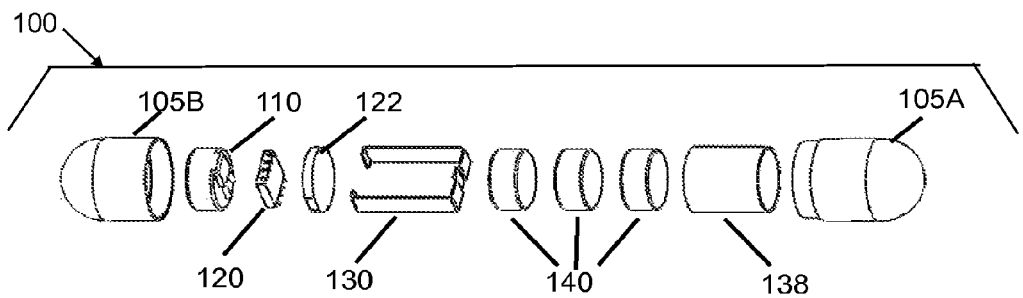
FIG. 1 is a schematic exploded view of a GIC according to some embodiments of the present invention.

The principles and operation of the inventive gastrointestinal capsules, and the treatment methods utilizing such capsules, may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

FIG. 1 is a schematic exploded view of a GIC 100 according to some embodiments of the present invention. GIC 100 may include a capsule housing or shell 105 (best seen in FIG. 2A) having complementary (e.g., male and female) components 105A, 105B. Within the capsule housing may be disposed a thrusting mechanism that may include a motor 110 and a circuit board 122 having a CPU, microprocessor or controller 120. Within the capsule housing may further be disposed a power supply such as at least one battery 140, an electrically conductive bridge such as metal bridge 130, and an insulator 138.

Figure 2A:
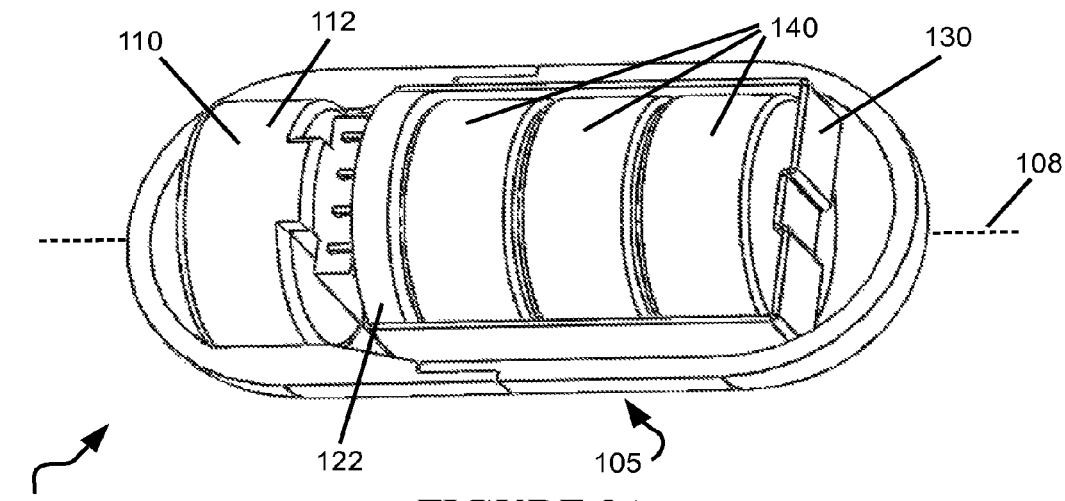
FIG. 2A is a cut-open, perspective view of the GIC provided in FIG. 1.

A cut-open, perspective view of GIC 100 is provided in FIG. 2A. Three disc-shaped batteries 140 and circuit board 122 may be held together by metal bridge 130. Bridge 130 may be adapted to make electrical contact with a broad face of the battery distal to circuit board 122, and may provide power to circuit board 122. Batteries 140 may also power motor 110, e.g., via conducting wires (not shown) attached to circuit board 122.

The thrusting mechanism may be adapted to deliver to exert radial forces on capsule housing 105. In one embodiment, motor 110 is an eccentric motor having an eccentric weight 112. As motor 110 spins in a generally normal fashion with respect to a longitudinal axis 108 of GIC 100, radial forces are exerted on housing 105.

Figure 2B:
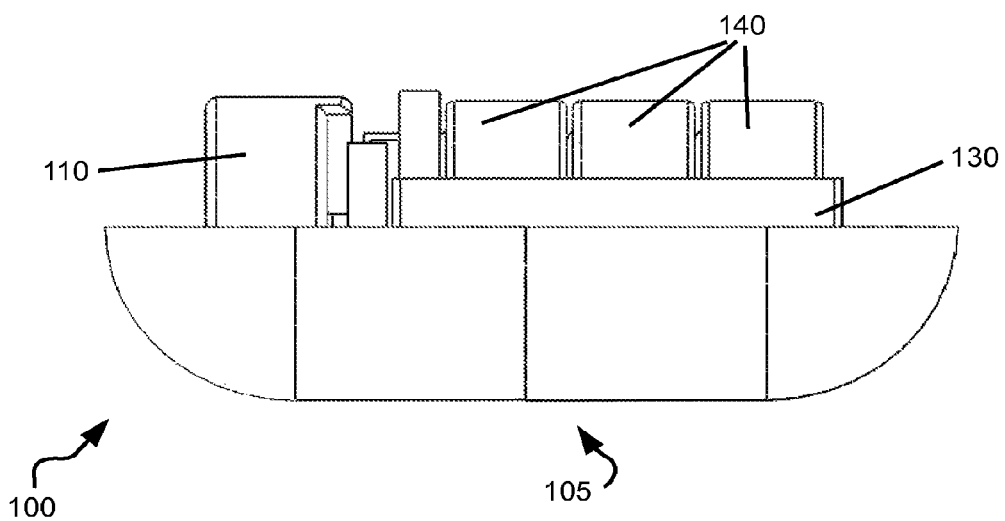
FIG. 2B is a side view of the cut-open GIC of FIG. 2A.

A side view of the cut-open GIC 100 is provided in FIG. 2B.

The inventive GIC is adapted such that, after ingestion thereof, the GIC is carried by bodily forces through the upper and lower gastrointestinal tracts. Ultimately, the GIC may be naturally evacuated along with the stool.

In accordance with some embodiments of the present invention is provided the GIC may be adapted to repeatedly vibrate within the gastrointestinal walls of the user. The GIC may be automatically activated at a predefined time following ingestion. Similarly, a timing mechanism of (or associated with) CPU 120 may be initiated at, or prior to, ingestion.

In accordance with some embodiments of the present invention, activation of the GIC may be set to automatically occur 2 to 12 hours, 2 to 10 hours, or 2 to 8 hours following ingestion, and more typically, 6 to 10 hours or 6 to 8 hours following ingestion. Such a (typically pre-determined) time delay may match the transit time in which the GIC reaches the large bowel via the upper gastrointestinal tract. The transit time within the large bowel may be significantly longer, in the range of 2 to 5 days, depending on whether the transit time is normal or prolonged, as in cases of constipation. In such cases, the time delay for activation may range between 6 and 24 hours.

Once activated, the inventive GICs may be adapted to agitate for at least 15 minutes, at least 30 minutes, at least 1 hour, at least 1.5 hours, at least 2 hours, at least 2.5 hours, or at least 3 hours, including intermittent periods of rest. Typically, the inventive GICs may be adapted to agitate for less than 8 hours, including intermittent periods of rest.

Figure 3A:
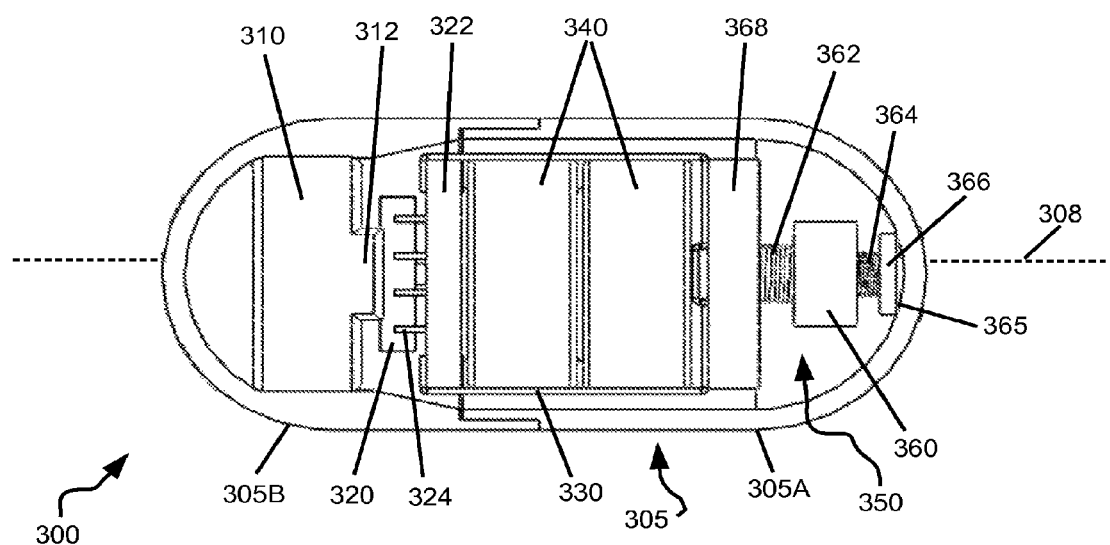
FIG. 3A is a schematic, top view of a cut-open GIC according to some embodiments of the present invention.

FIG. 3A is a schematic, top view of a cut-open GIC 300 according to some embodiments of the present invention. GIC 300 may include a capsule housing or shell 305 having complementary components 305A, 305B. Within capsule housing 305 may be disposed a thrusting mechanism that may include a motor 310 and a circuit board 322 having a CPU, microprocessor or controller 320. Within the capsule housing may further be disposed a power supply such as at least one battery 340, and an electrically conductive bridge such as metal bridge 330. An insulating barrier (shown in FIG. 1) may be disposed between battery 340 and bridge 330, to avoid short-circuiting.

As shown in FIG. 3A, two (by way of example) disc-shaped batteries 340 and circuit board 322 may be held together by metal bridge 330. Bridge 330 makes electrical contact with a broad face of the battery distal to circuit board 322, and may provide power to circuit board 322. Batteries 340 may also power motor 310, e.g., via conducting wires (not shown) attached to circuit board 322. Microprocessor or controller 320 may be mechanically and electrically attached to circuit board 322 by means of electrically conductive connectors 324.

As described hereinabove, the thrusting mechanism may be adapted to exert eccentric or radial forces on capsule housing 305. The motor may be an eccentric motor having an eccentric weight 312. As motor 310 spins in a generally normal fashion with respect to a longitudinal axis of GIC 300, radial forces are exerted on housing 305.

GIC 300 may be equipped with an auxiliary axial perturbation arrangement such as axial perturbation arrangement 350, adapted to effect axial forces on housing 305. The axial perturbation arrangement may be part of the thrusting mechanism. In the exemplary embodiment provided in FIG. 3A, perturbation arrangement 350 includes a motor 368 that is electrically connected to batteries 340. Motor 368 may be disposed at a distal end of GIC 300, with respect to motor 310.

Axial perturbation arrangement 350 may further include a motor screw or screw shaft such as axial motor screw shaft 364, mechanically associated with, and driven by, motor 368, and aligned in a generally axial fashion within GIC 300, typically along, generally along, or parallel to a longitudinal axis 308 of the capsule; a spring 362, which may be concentrically disposed on shaft 364, proximal to motor 310; a weight 360, which may be aligned in an axial fashion within GIC 300, and which may typically be disposed between spring 362 and motor screw 364; a stopper 366, adapted to receive a distal end (with respect to motor 310) of motor screw 364, and impinging against an inner wall 365 of capsule housing 305.

Figure 3B:
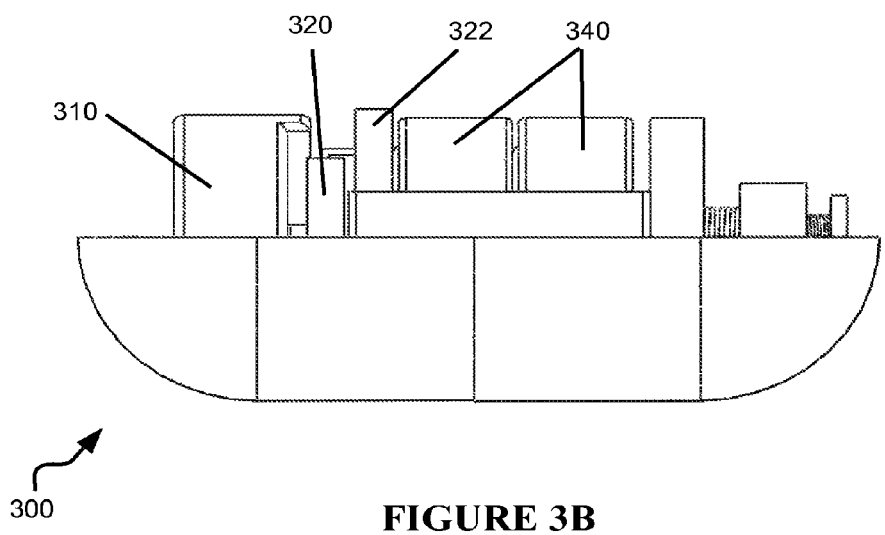
FIG. 3B is a side view of the cut-open GIC of FIG. 3A.

A side view of cut-open GIC 300 is provided in FIG. 3B.

Figure 3C:
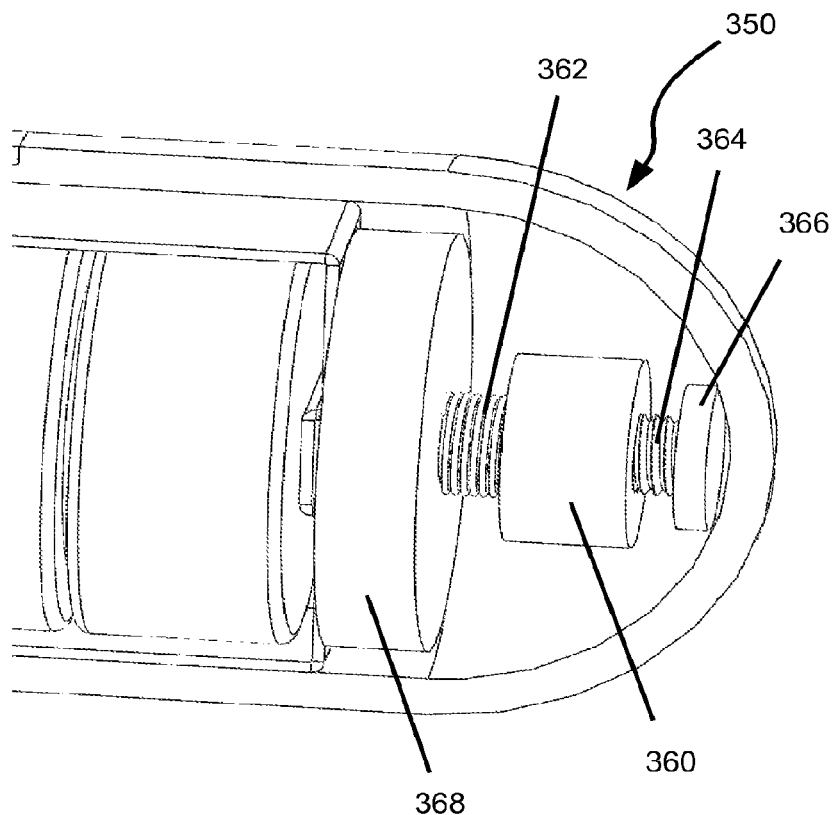
FIG. 3C is a partial perspective view of the cut-open GIC of FIG. 3A.

FIG. 3C is a partial view of cut-open GIC 300, showing a magnified perspective view of perturbation arrangement 350, according to one embodiment of the invention.

Figure 3D:
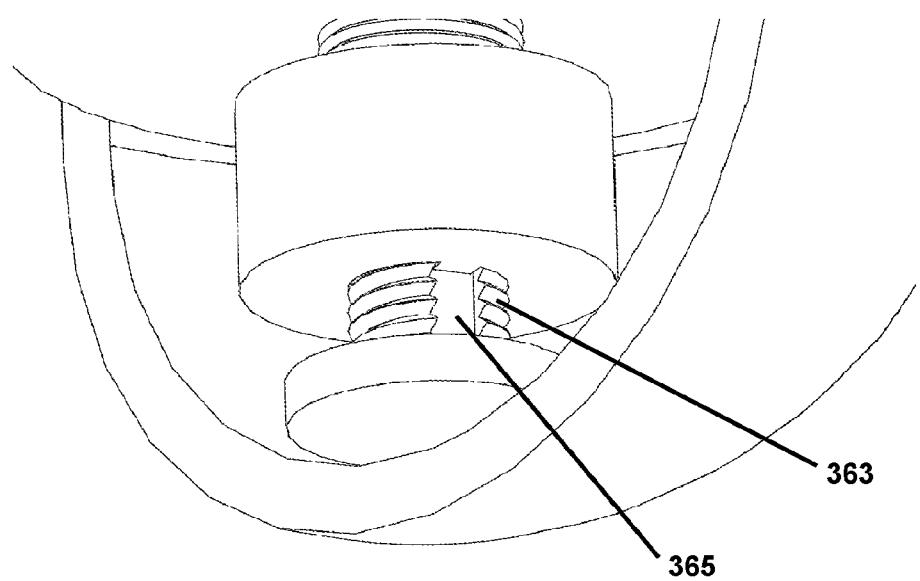
FIG. 3D is another partial view of cut-open GIC 300, showing a magnified perspective view of an external interrupted thread of screw shaft, according to one embodiment of the invention.
Figure 4A:
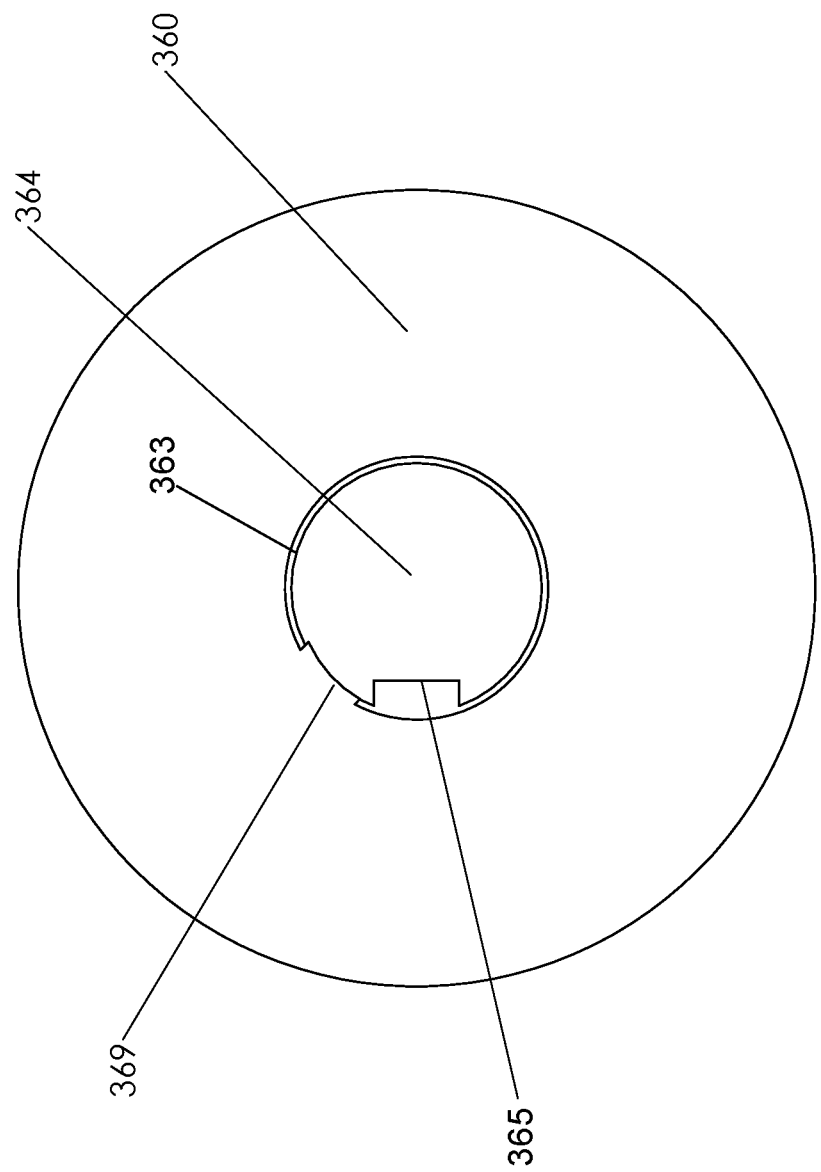
FIG. 4A is a sectional illustration of a screw shaft and a weight forming part of GIC 300 in a first state, according to an embodiment of the invention.
Figure 4B:
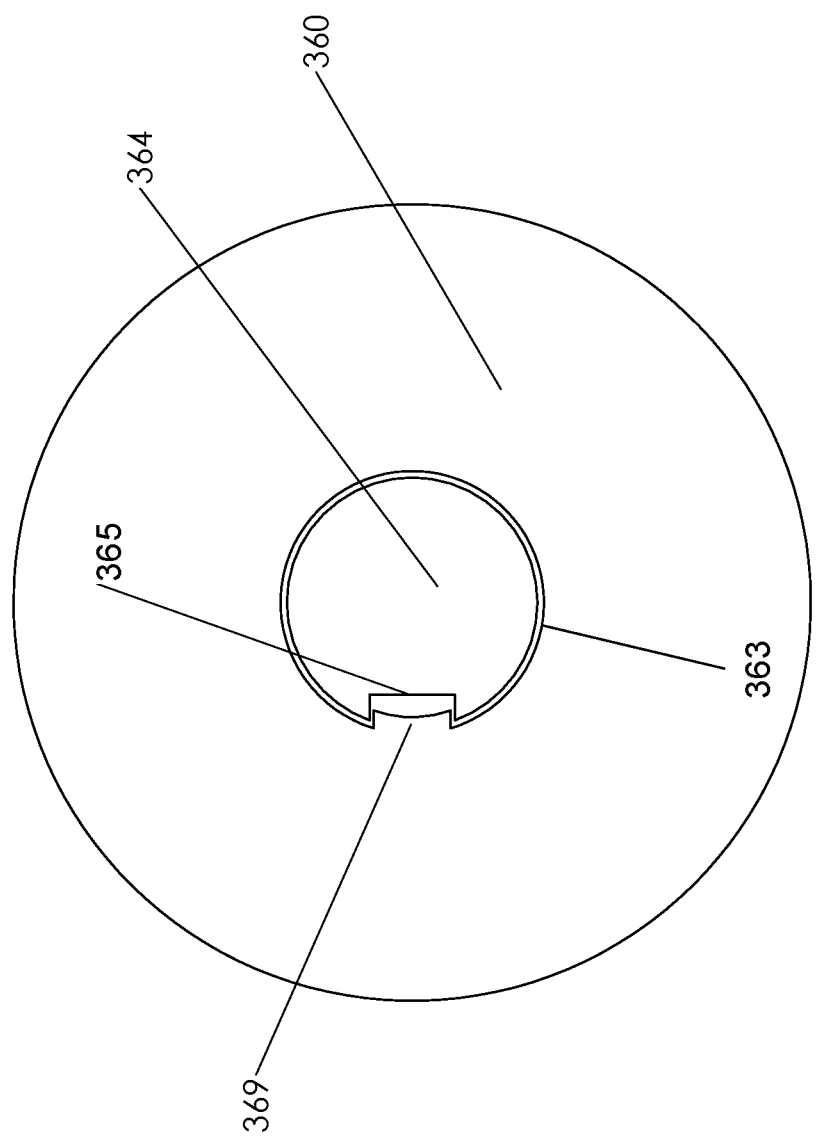
FIG. 4B is a sectional illustration of the screw shaft and the weight of FIG. 4A, in a second state, according to an embodiment of the invention.
Figure 4C:
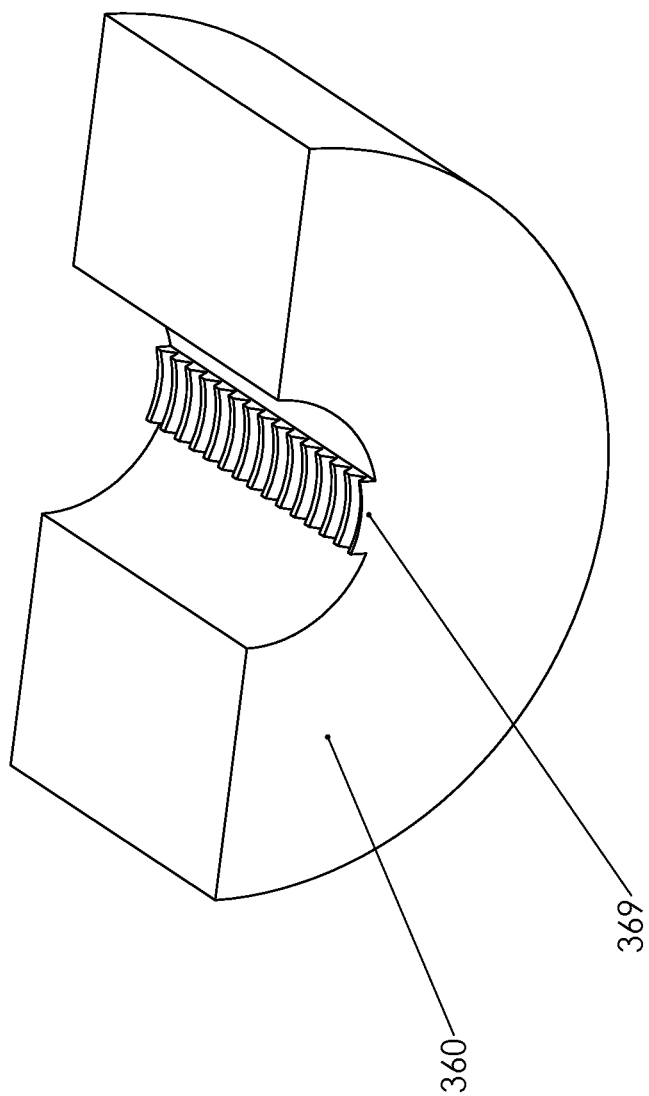
FIG. 4C is a sectional perspective view of the weight of FIGS. 4A and 4B.

FIG. 3D is another partial view of cut-open GIC 300, showing a magnified perspective view of an external interrupted thread 363 of screw shaft 364, according to one embodiment of the invention. Weight 360, which may be generally of an annular shape, may advantageously have a threaded internal surface 369, shown clearly in FIG. 4C, that may be generally circumferentially complementary to the threading of interrupted thread 363. The interrupted portion 365 of interrupted thread 363 may have a twin interrupted portion on the (radially and longitudinally) opposite side of screw shaft 364.

In one exemplary mode of operation of perturbation arrangement 350, screw shaft 364, driven by motor 368, engages the threaded internal surface 369 of weight 360, such that weight 360 is drawn towards spring 362, and compression of spring 362 ensues ("State 1"). As screw shaft 364 continues to turn, the interrupted portion 365 of interrupted thread 363 meets the threaded internal surface 369 of weight 360, as seen clearly in FIG. 4B, whereupon weight 360 becomes disengaged and longitudinally free with respect to interrupted thread 363 of shaft 364. Spring 362, disposed in a compressed position, is now free to longitudinally extend ("State 2"), forcefully urging weight 360 towards stopper 366, and thereby axially impacting capsule housing 305. As screw shaft 364 continues to turn, screw shaft 364 again engages the threaded internal surface 365 of weight 360, whereby perturbation arrangement 350 again reassumes State 1.

We have found that the ratio of the radial forces exerted to the axial forces exerted, on the housing, may be at least 1:1, at least 1.25:1, or at least 1.5:1, and more typically, at least 2:1, at least 3:1, at least 4:1, or at least 5:1.

Without wishing to be bound by theory, the inventor believes that the radial forces provide the primary effect of stimulating the walls of the lower gastrointestinal tract. Nonetheless, the axial forces may be useful in the locomotion of the capsule, particularly in regions that are partially clogged or blocked by chyme. Since the power supply is limited, a relatively high ratio of the radial forces exerted to the axial forces exerted may be critical in delivering the requisite stimulation to the walls of the tract.

The ratio of forces may be defined as the sum of the radial forces delivered to the sum of the axial forces delivered, over the entire time of activity of the GIC. For a GIC having a substantially repeating period, the ratio of forces may be defined as the sum of the radial forces delivered to the sum of the axial forces delivered, over one complete period.

In one embodiment, the GIC may be introduced to the body of the user via oral insertion.

In one embodiment, the GIC may be introduced into a lower end of the large intestine via the rectal opening. The general procedure may be similar to the introduction of a suppository. A first end of the GIC, which may have a tapered shape, and may be lubricated, may be placed at the rectal opening and gently pushed into the rectum. The GIC may be manually urged up the rectal tract, to a distance of several centimeters and up to about eight centimeters from the rectal opening. Deeper insertion, to the end of the rectum distal to the rectal opening, may be achieved by means of an insertion apparatus. Such an apparatus may include a long, smooth rod, preferably made of, or coated with, a flexible, smooth, biocompatible substance such as silicone. At a first end of the apparatus may be disposed a securing mechanism adapted to secure the GIC until the GIC has reached the desired position within the rectum, and a release mechanism adapted to release the GIC, upon demand. The securing and release mechanism may include a spring. Such an apparatus, whose structure or structures will be readily apparent to those of ordinary skill in the art, may enable the introduction of the GIC through the rectal tract, to a position of at least 8 cm, at least 10 cm, at least 12 cm, or at least 14 cm from the rectal opening.

In an actual capsule prototype, the capsule length was 24.2 mm, and the capsule diameter was 11.3 mm. The shell was made of medical Makrolon® 2458, a biocompatible material. The voltage was 4.5 Volts.

Following ingestion of the capsule, the vibrating sequence begins after a predetermined amount of time (delay). This delay (6 or 8 hours) may allow the capsule to reach the large intestine before the vibrating sequence is initiated.

The capsule may be activated by an electromagnetic signal carrying an activation code. The activation may be confirmed, e.g., by vibration of the capsule (e.g., 3 consecutive vibrations), or by any of various visual (e.g., LED) or audio signals, to ensure that the output (or the programming result) is identical to the requirements indicated by the physician.

The capsule typically contains an electromechanical system that operates a mechanically controlled vibrating mechanism adapted to induce peristaltic wave activity in the large intestine. A computerized algorithm may provide the vibration rate and relaxation period in order to prevent habituation.

Various therapeutic modes may be pre-programmed or pre-set for the GIC. For example:

Mode A: activation delay is set to 8 hours. The vibration rate is 180 vibration cycles per hour, each cycle consisting of 4 seconds of a vibration period and 16 seconds of a repose (relaxation) period, corresponding, on a per hour basis, to 12 minutes of vibration periods and 48 minutes of rest intervals or periods.

Mode B: activation delay is set to 6 hours. The vibration rate is 240 vibration cycles per hour, each cycle consisting of 4 seconds of a vibration period and 11 seconds of a repose period, corresponding, on a per hour basis, to 16 minutes of vibration periods and 44 minutes of rest intervals or periods.

To ensure that the capsule has reached the large intestine, the capsule is equipped with an activation delay mechanism (typically having a pre-determined delay of 6-8 hours) that defines the time period between activation (and typically, ingestion) and the initial onset of the vibrating phase.

The capsule may be advantageously activated by qualified medical personnel. In some cases, the capsule may be activated by the user.

In some embodiments of the present invention, various dedicated GI capsules may be produced, that may be pre-programmed according to the needs of various patients. Such embodiments may not require the transmitter and antenna.

In some embodiments employing programming according to the needs of the patient:

A. The capsule may be equipped with an electronic circuit, transmitter and antenna, adapted to receive an external signal regarding the mode of activation required.

B. The capsule may be activated via a dedicated base unit. The base unit may include an electronic circuit, a power supply (batteries), software and a socket adapted to receive the capsule. The base unit has various programming modes that enable the medical personnel to select the appropriate one according to the specific needs of the patient/user, e.g., according to the severity of the constipation (e.g., Rome II, Rome III, etc.).

C. The activation of the capsule with the selected mode of operation may be performed by the dedicated base unit, which may transmit to the capsule the programmed mode, by a simple push of a button on the base unit.

D. The capsule may be adapted to signal that receipt of the mode of work chosen, and after this signal, the capsule may be activated and may then be ready to be swallowed.

The GICs of the present invention are effective in treating various levels of functional constipation, including Rome I, Rome II and Rome III criteria (severity) levels. The GICs of the present invention may be effective in treating more serious levels/criteria of constipation.

The GICs of the present invention have been found to be effective in relieving functional constipation accompanied by abdominal pain, such as irritable bowel syndrome with constipation (IBS-C).

The GICs of the present invention have been found to be effective in relieving functional constipation, such as chronic idiopathic constipation (CIC).

The Rome III criteria for functional constipation are provided below.

Rome III diagnostic criteria for functional constipation, based on: *ROME III: The Functional Gastrointestinal Disorders, Third Edition* (*October,* 2006)

1. Must include two or more of the following:
   a. Straining during at least 25% of defecations
   b. Lumpy or hard stools in at least 25% of defecations
   c. Sensation of incomplete evacuation for at least 25% of defecations
   d. Sensation of anorectal obstruction/blockage for at least 25% of defecations
   e. Manual maneuvers to facilitate at least 25% of defecations (e.g., digital evacuation, support of the pelvic floor)
   f. Fewer than three defecations per week
2. Loose stools are rarely present without the use of laxatives
3. Insufficient criteria for irritable bowel syndrome
* Criteria fulfilled for the last 3 months with symptom onset at least 6 months prior to diagnosis The Rome II diagnostic criteria for functional constipation are similar, but the timeframe is more relaxed: at least 12 weeks, which need not be consecutive, in the preceding 12 months.

According to one aspect of the present invention there is provided a method for mechanically stimulating a wall of a segment of a mammalian gastrointestinal tract of a user by means of a gastrointestinal capsule, the method including the steps of: (a) providing at least one capsule (preferably any one of the capsules disclosed herein); and (b) administering at least one treatment session, each treatment session including: (i) delivering the gastrointestinal capsule into the tract; and (ii) effecting activation of a thrusting mechanism of the gastrointestinal capsule to achieve mechanical stimulation of the wall of the gastrointestinal tract.

The at least one treatment session may advantageously include a plurality of treatment sessions. Typically, at least one of the treatment sessions is administered per week, over a treatment period extending for at least two weeks, at least three weeks, at least four weeks, at least five weeks, at least six weeks, or at least eight weeks. At least 1.5, at least 1.75, at least 2, at least 2.5, or at least 3 of the treatment sessions may be administered per week of the treatment period.

In some embodiments, the frequency of the treatment sessions administered to the user is within a range of 1.5 to 7 per week of the treatment period.

In some embodiments, the frequency is within a range of 1 to 7, 1.5 to 6, 1.5 to 7, 1.5 to 6, 1.5 to 5, 1.5 to 4, 1.5 to 3.5, 1.5 to 3, 2 to 6, 2 to 5, 2 to 4, 2 to 3.5, or 2 to 3, per week of the treatment period.

In some embodiments, within each treatment session, the activation of the thrusting mechanism is performed for a duration effective to achieve mechanical stimulation of the wall of the gastrointestinal tract.

In some embodiments, within each treatment session, the activation of the thrusting mechanism is performed for a duration effective to increase a frequency of spontaneous bowel movements of the user.

In some embodiments, within each treatment session, the activation of the thrusting mechanism is performed for a duration effective to increase a frequency of spontaneous bowel movements of the user by at least 25%, at least 50%, at least 75%, or at least 100%.

In some embodiments, within each treatment session, the activation of the thrusting mechanism is performed is performed for a duration effective to at least partially relieve a condition of constipation of the user.

In some embodiments, within each treatment session, the activation of the thrusting mechanism is performed for a duration effective to completely relieve a condition of constipation of the user.

EXAMPLE

Reference is now made to the following example, which together with the above description, illustrate the invention in a non-limiting fashion.

Clinical trials on patients were performed using the GIC described with reference to FIGS. 1, 2A and 2B.

The study included 22 subjects, 2 males and 20 females, aged between 19 to 65 years, who were found to be appropriate for the study. 20 subjects completed the study according to the protocol, 2 subjects withdrew their consent.

Patients were followed for 14 days on their normal bowel movement and medication consumption. After 14 days the first capsule was administered and extraction of the capsule was confirmed up to day 21 in the study. During this week, the patient was followed to eliminate safety concerns. Once the first capsule extraction was confirmed, the patients were invited to the clinic twice a week for capsule administration and follow-up. During the bi-weekly visits, a capsule was activated by the study nurse and administered. Prior capsule extraction was verified using a stool collection kit.

During these visits, satisfactory improvement of the symptoms/condition was assessed by the patient.

After the initial, two-week baseline period, in which the number of spontaneous bowel movements was recorded, the GIC was administered about twice per week for a period of close to 7 weeks.

The activation delay of the capsules was set to 8 hours. The vibration rate was 180 vibration cycles per hour, each cycle consisting of 4 seconds of a vibration period and 16 seconds of a repose period. The motor operated at 12,000 RPM (200 Hz), such that the thrusting mechanism exerted radial forces on the capsule housing at a vibration frequency of about 27 Hz. The average force exerted by the vibrations was 64 grams force (gf), while the maximal (instantaneous) force exerted was about 176 gf.

Following the activation delay, the therapeutic treatment was conducted for about 2-2.5 hours.

Efficacy was assessed by the increase in spontaneous bowel movements per week during the 7.5 weeks of treatment, as compared to a two-week baseline period. The efficacy assessment was performed for the Per Protocol population.

All tests applied were two-tailed, and p value of 5% or less was considered statistically significant. The data was analyzed using SAS® version 9.1 for Windows (SAS Institute, Cary, N.C.).

An increase in the mean number of spontaneous bowel movements per week was observed (see Table 1). This increase was found to be statistically significant (Mean increase=1.78, Standard deviation=1.09, p<0.001), as shown in Table 2.

The mean number of spontaneous bowel movements per week of the treatment program is provided in Table 3.

After the 7.5 weeks of treatment, 20% of the subjects no longer exhibited the Rome III criteria for CIC. For the group as a whole (20 subjects), the average number of idiopathic constipation criteria was reduced from 5.5 (out of 6 total) to 3.2 (p<0.001). 50% of the subjects displayed a higher number of bowel movements, on a weekly basis, and 67% of the subjects exhibited improved parameters regarding stool hardness and straining at defecation.

Following the study, the status of the patients was monitored for a period of 6 months. With regard to constipation, it was found that after this six-month period, over 40% of the patients continued to enjoy an improved situation, while the situation of about 90% of the patients was better or unchanged.

With regard to the CIC group of subjects (10 in all), after the 7.5 weeks of treatment, 2 of the subjects (20%) no longer exhibited the Rome III criteria for CIC. Within the CIC group, the average number of idiopathic constipation criteria was reduced from 5.7 to 3.2 (p≤0.004). 50% of the subjects displayed a higher number of bowel movements, on a weekly basis, and 80% of the subjects exhibited improved parameters regarding straining at defecation.

With regard to the C-IBS group of subjects (10 in all), after the 7.5 weeks of treatment, 5 of the subjects (50%) no longer exhibited the Rome III criteria for C-IBS. Within the C-IBS group, 3 of the subjects (30%) experienced reduced abdominal pain.

TABLE 1

| Site | Subject | 2 weeks baseline | Treatment period | Change | Change (%) |
|---|---|---|---|---|---|
| 1 | 1 | 2.50 | 5.40 | 2.90 | 116% |
|  | 2 | 2.00 | 2.33 | 0.33 | 15% |
|  | 3 | 1.00 | 3.43 | 2.43 | 240% |

TABLE 1-continued

| Site | Subject | 2 weeks baseline | Treatment period | Change | Change (%) |
|---|---|---|---|---|---|
| | 4 | 2.00 | 4.34 | 2.34 | 117% |
| | 5 | 2.50 | 3.50 | 1.00 | 40% |
| | 6 | 2.50 | 2.33 | −0.17 | −8% |
| | 7 | 1.50 | 3.50 | 2.00 | 133% |
| | 8 | 2.50 | 2.63 | 0.13 | 5% |
| | 9 | 3.23 | 6.43 | 3.20 | 103% |
| | 10 | 2.00 | 2.63 | 0.63 | 32% |
| | 13 | 3.27 | 5.36 | 2.10 | 64% |
| | 14 | 1.00 | 1.96 | 0.96 | 96% |
| | 18 | 3.50 | 6.00 | 2.50 | 71% |
| | 19 | 2.69 | 4.25 | 1.56 | 58% |
| | 22 | 2.00 | 4.90 | 2.90 | 145% |
| | 26 | 3.00 | 4.00 | 1.00 | 33% |
| | 27 | 1.00 | 2.20 | 1.20 | 120% |
| 2 | 3 | 2.33 | 5.10 | 2.77 | 119% |
| | 4 | 2.00 | 4.38 | 2.38 | 119% |
| | 6 | 1.65 | 5.13 | 3.49 | 212% |

TABLE 2

| Mean Number of Spontaneous bowel movements per period | 2 weeks baseline | Treatment period | Change |
|---|---|---|---|
| Mean | 2.21 | 3.99 | 1.78 |
| Std | 0.74 | 1.36 | 1.09 |
| Min | 1.00 | 1.96 | −0.17 |
| Median | 2.17 | 4.13 | 2.05 |
| Max | 3.50 | 6.43 | 3.49 |
| P | | | <0.001 |

TABLE 3

| Mean Number of Spontaneous bowel movements per week | Baseline | | Treatment | | | | | | |
|---|---|---|---|---|---|---|---|---|---|
| | 1st week | 2nd week | 1st week | 2nd week | 3rd week | 4th week | 5th week | 6th week | 7th week |
| Mean | 2.30 | 2.30 | 4.05 | 3.30 | 3.80 | 4.20 | 4.85 | 4.05 | 3.65 |
| Std | 1.34 | 1.08 | 1.85 | 1.26 | 1.85 | 2.31 | 2.21 | 2.04 | 1.93 |
| Min | 1.0 | 1.0 | 1.0 | 1.0 | 1.0 | 1.0 | 2.0 | 1.0 | 1.0 |
| Median | 2.0 | 2.0 | 3.5 | 3.0 | 3.0 | 4.0 | 5.5 | 4.0 | 3.5 |
| Max | 7.0 | 5.0 | 7.0 | 6.0 | 7.0 | 12.0 | 8.0 | 8.0 | 7.0 |

*Last Observation Carry Forward (LOCF): for patients with no data or missing data on 7th treatment week, their data from 6th treatment week was taken as final observation.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A gastrointestinal capsule (GIC) comprising:
   (a) a capsule housing having a longitudinal axis;
   (b) a thrusting mechanism, disposed within said capsule housing, said thrusting mechanism having an active mode, and a passive mode with respect to said active mode,
   said thrusting mechanism including:
      (i) a rotatably mounted eccentric weight,
         said thrusting mechanism adapted, in said active mode, to rotate said eccentric weight thereby to exert radial forces on said capsule housing, in a radial direction with respect to said longitudinal axis, and
      (ii) an axial perturbation arrangement including:
         a motor;
         a motor shaft, disposed at least partially in a direction along said longitudinal axis, said motor shaft operatively connected to, and driven by, said motor; and
         a thrusting weight associated with said motor shaft,
         said axial perturbation arrangement adapted to at least periodically urge said thrusting weight along said motor shaft, to deliver axial forces to said capsule housing,
   such that when the gastrointestinal capsule is disposed within a gastrointestinal tract of a user, and said thrusting mechanism is in said active mode, the gastrointestinal capsule stimulates a wall of said gastrointestinal tract; and
   (c) a battery adapted to power said thrusting mechanism.

2. The GIC of claim 1, wherein:
   said active mode includes a series of at least two pulses of said radial forces, said series having a first duration;
   said passive mode has a second duration;
   an activation cycle is defined by said series of pulses followed by said second duration;
   said first duration is within a range of 1-10 seconds; and
   said second duration exceeds said first duration.

3. The GIC of claim 2, said activation cycle having a period within a range of 5-60 seconds.

4. The GIC of claim 2, said activation cycle having a period within a range of 8-30 seconds.

5. The GIC of claim 2, said thrusting mechanism configured such that said first duration is within a range of 2.5-6 seconds.

6. The GIC of claim 1, said thrusting mechanism configured to exert said radial forces on said capsule housing to attain a vibrational frequency within a range of 12 Hz to 80 Hz.

7. The GIC of claim 6, said thrusting mechanism configured such that said vibrational frequency is within a range of 15 Hz to 50 Hz.

8. The GIC of claim 6, said thrusting mechanism configured such that said vibrational frequency is within a range of 18 Hz to 45 Hz.

9. The GIC of claim 1, said thrusting mechanism configured such that a net force exerted by the gastrointestinal capsule on an external environment thereof is in the range of 400-600 grams force.

10. The GIC of claim 1, said thrusting mechanism configured such that an instantaneous net force exerted by the gastrointestinal capsule on an external environment thereof is in the range of 800-1500 grams force.

11. The GIC of claim 1, said thrusting mechanism including a controller, electrically attached to said battery, said controller adapted to control said thrusting mechanism.

12. The GIC of claim 1, wherein a ratio of said radial forces to said axial forces is at least 1.5:1.

13. The GIC of claim 12, said ratio of said radial forces to said axial forces being at most 20:1.

14. The GIC of claim 12, said ratio of said radial forces to said axial forces being within a range of 2.5:1 to 15:1.

15. The gastrointestinal capsule of claim 1, said axial perturbation arrangement further including a stopper or cap, adapted to receive a distal end of said motor shaft, said stopper or cap impinging against an inner wall of said capsule housing.

16. The gastrointestinal capsule of claim 1, said axial perturbation arrangement further including a spring associated with said motor shaft,
said axial perturbation arrangement adapted such that, in a first state, said spring is compressed, and in a second state, said spring is released against said thrusting weight, to urge said thrusting weight along said motor shaft, to deliver said axial forces to said capsule housing.

17. The gastrointestinal capsule of claim 16, said motor shaft passing through said thrusting weight, said motor shaft having an external interrupted thread, and said thrusting weight having a threaded internal surface generally circumferentially complementary to a threading of said external interrupted thread,
whereby, in said first state, said external interrupted thread engages said threaded internal surface, and in said second state, said threaded internal surface is disengaged and longitudinally free with respect to said external interrupted thread.

18. The gastrointestinal capsule of claim 16, said motor shaft passing through said thrusting weight, said thrusting weight adapted to turn with said motor shaft, said motor shaft having an external interrupted thread, and said thrusting weight having a threaded internal surface generally circumferentially complementary to a threading of said external interrupted thread,
said axial perturbation arrangement further adapted such that in said first state, said external interrupted thread engages said threaded internal surface to compress said spring, and in said second state, said threaded internal surface is disengaged and longitudinally free with respect to said external interrupted thread, such that said spring is released against said thrusting weight.

19. A gastrointestinal capsule (GIC) comprising:
(a) a capsule housing having a longitudinal axis;
(b) a thrusting mechanism, disposed within said capsule housing, said thrusting mechanism having an active mode, and a passive mode with respect to said active mode,
said thrusting mechanism including:
(i) a rotatably mounted eccentric weight,
said thrusting mechanism adapted, in said active mode, to rotate said eccentric weight thereby to exert radial forces on said capsule housing, in a radial direction with respect to said longitudinal axis, and
(ii) an axial perturbation arrangement including:
a motor;
a motor shaft, disposed at least partially in a direction along said longitudinal axis, said motor shaft operatively connected to, and driven by, said motor; and
a thrusting weight associated with said motor shaft,
said axial perturbation arrangement adapted to at least periodically urge said thrusting weight along said motor shaft, to deliver axial forces to said capsule housing,
such that when the gastrointestinal capsule is disposed within a gastrointestinal tract of a user, and said thrusting mechanism is in said active mode, the gastrointestinal capsule stimulates a wall of said gastrointestinal tract; and
(c) a battery adapted to power said thrusting mechanism;
said active mode including a series of at least two pulses of said radial forces, said series having a first duration, said passive mode having a second duration,
wherein an activation cycle is defined by said series of pulses followed by said second duration, and wherein said first duration is within a range of 1-10 seconds.

* * * * *